United States Patent [19]

Tsuru et al.

[11] Patent Number: 5,055,307
[45] Date of Patent: Oct. 8, 1991

[54] SLOW RELEASE DRUG DELIVERY GRANULES AND PROCESS FOR PRODUCTION THEREOF

[75] Inventors: Sumiaki Tsuru, Tokyo; Masashi Tsugita, Tokorozawa; Ken Takasaki, Tokyo; Akihiko Yokoo, Tokyo; Takeshi Ichitsuka, Tokyo, all of Japan

[73] Assignee: Asahi Kagaku Kogyo Kabushiki Kaisha, Japan

[21] Appl. No.: 458,310

[22] Filed: Dec. 28, 1989

[30] Foreign Application Priority Data

Dec. 29, 1988 [JP] Japan ................ 63-335355

[51] Int. Cl.$^5$ ................................. A61K 9/16
[52] U.S. Cl. ..................... 424/493; 424/502; 424/496; 424/497; 424/498; 424/499; 424/500; 424/501
[58] Field of Search .......... 435/243; 423/309; 210/266; 424/498, 602, 468, 490, 443, 499, 493, 496, 497, 500, 501, 502

[56] References Cited

U.S. PATENT DOCUMENTS

| | | | |
|---|---|---|---|
| 4,322,398 | 3/1982 | Reiner et al. | |
| 4,341,759 | 7/1982 | Bogentoft | 424/498 |
| 4,675,188 | 6/1987 | Chu | 424/602 |
| 4,707,361 | 11/1987 | Gustafson | 424/602 |
| 4,720,384 | 1/1988 | DiLuccio | 424/468 |
| 4,761,366 | 8/1988 | Nakajima | 435/243 |
| 4,781,904 | 11/1988 | Tagaya | 423/309 |
| 4,840,799 | 6/1989 | Appelgren | 424/498 |
| 4,865,733 | 9/1989 | Tsuru | 210/266 |
| 4,892,738 | 1/1990 | Takagishi | 424/468 |
| 4,935,247 | 6/1990 | Marttila | 424/498 |
| 4,937,080 | 6/1990 | Appelgren | 424/490 |

FOREIGN PATENT DOCUMENTS

| | | |
|---|---|---|
| 54-163807 | 12/1979 | Japan . |
| 58-157715 | 9/1983 | Japan . |
| 61-47401 | 3/1986 | Japan . |
| 62-6522 | 2/1987 | Japan . |

OTHER PUBLICATIONS

Copy of Australian Patent Abstract AU-A-10240/83.
An English language abstract of Japanese Unexamined Patent Publication No. 61-47401.
An English language abstract of Japanese Unexamined Patent Publication No. 55-122710.

*Primary Examiner*—Thurman K. Page
*Assistant Examiner*—William E. Benston, Jr.

[57] ABSTRACT

Slow release drug delviery granules comprising porous granules of a calcium phosphate compound having an atomic ratio of Ca to P of 1.3 to 1.8, a porosity of 0.1 to 70%, a specific surface area of 0.1 to 50 m$^2$/g and a pore size of 1 nm to 10 μm, fired at a temperature of 200° to 1400° C., and a drug component impregnated in pores of the granules, and a process for producing the same. The drug delivery granules of the present invention have a controllable, prolonged effect of drug release and a good imaging property to an X-ray or ultrasonic wave, and therefore can be advantageously utilized in the field of chemotherapy.

16 Claims, 4 Drawing Sheets

SLOW RELEASE DRUG DELIVERY GRANULES AND PROCESS FOR PRODUCTION THEREOF

BACKGROUND OF THE INVENTION

1. Field of the Invention

The present invention relates to a drug delivery granule, more particularly, a drug delivery granule capable of slowly releasing impregnated drug components therefrom. Since the drug delivery granule of the present invention has a controllable and good prolonged effect of the drug release and a good imaging property to an X-ray or ultrasonic wave, it can be advantageously used in fields such as chemotherapy. The present invention also relates to a process for the production of such a drug delivery granule.

2. Description of the Prior Art

In the field of a chemotherapy, it has been desirable to provide slow release drugs which can exhibit a prolonged effect or action thereof for the longest possible period. In particular, since transvascular chemotherapy has recently been developed, and is effectively used to treat hepatoma or similar tumors, researchers are studying slow release drugs which are effective for transvascular chemotherapy.

For use in chemotherapy, several types of slow release drugs are well-known. Typical examples of prior art slow release drugs include a sponge preparation comprising sponge-like particles of the substance originated from an organism, such as gelatin or the like, and a drug component impregnated in the particles, or a suspension of drug particles in a fatty oil such as LIPIODOL (trade name of an ethyl ester of iodized poppy seed oil fatty acid; commercially available from Kodama K. K.). However, these drug particles suffer from many drawbacks such that the drug is not concentrated on a site to be treated due to unevenness of the size of the particles; that the length of the effect of the drug is not satisfactory because the drug is easily diffused in and absorbed by a living body; and that, after application, the drug can not be traced because it has no imaging property to the X-ray or ultrasonic wave.

Further, Japanese Unexamined Patent Publication (Kokai) No. 60-106459 discloses that a calcium phosphate-based filler containing an antibiotic substance can be produced by coating beads of a combustible substance with calcium phosphate, piercing the coated beads to open small holes therein, firing the beads to remove the combustible substance and filling the obtained hollow beads with the antibiotic substance through the hole of the bead wall. After filling of the antibiotic substance, the hole is closed or sealed to produce an antibiotic substance-containing filler. However, this production method is not suited for producing small size fillers, because it is essential to open a small hole in the bead wall. Only relatively larger fillers having a diameter of 2 to 40 mm can be produced. In addition, it requires troublesome operations such as filling of the antibiotic substance or sealing of the holes.

SUMMARY OF THE INVENTION

Therefore, an object of the present invention is to provide slow release drug delivery granules having a good imaging property to the X-rays or ultrasonic waves, and having a prolonged effect which can be controlled upon suitable selection of the porosity, specific surface area, pore size or the like of the porous granules used.

Another object of the present invention is to provide a process of easily producing the slow release drug delivery granules.

According to the present invention, these objects can be accomplished by porous granules of a calcium phosphate compound having an atomic ratio of Ca to P (Ca/P ratio) of 1.3 to 1.8, a porosity of 0.1 to 70%, a specific surface area of 0.1 to 50 $m^2/g$ and a pore size of 1 nm to 10 $\mu$m, fired at a temperature of 200° to 1400° C. A drug or medicine is contained in pores of the granules.

Further, according to the present invention, the slow release drug delivery granules can be produced by impregnating the above-described porous granules of a calcium phosphate compound with a drug component and drying the thus impregnated granules.

BRIEF DESCRIPTION OF THE DRAWINGS

The figures are graphs showing the results of measurements made in the working examples, in which.

DESCRIPTION OF THE PREFERRED EMBODIMENTS

Figure 1:
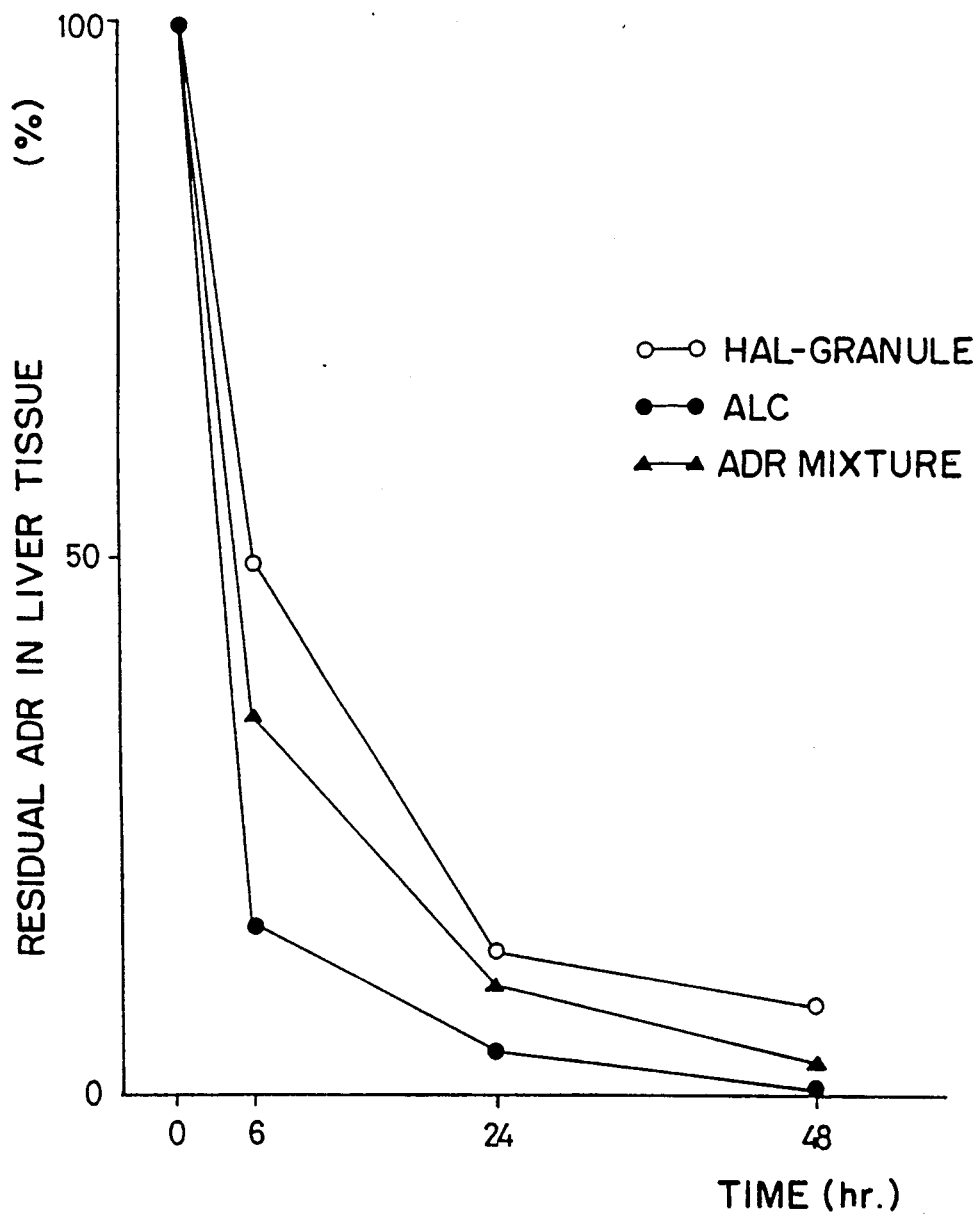
FIG. 1 is a graph showing a change of percentage of residual ADRIACIN (ADR) in the liver with time.

In the practice of the present invention, the calcium phosphate compound used as a starting material of the granules is not restricted, provided that it has a Ca/P ratio of 1.3 to 1.8. A Ca/P ratio of 1.35 to 1.75 is preferable, and a Ca/P ratio of 1.4 to 1.7 is more preferably. Typical examples of the calcium phosphate compound useful in the invention include α-or β-tricalcium phosphate, tetracalcium phosphate, different types of apatites such as hydroxyapatite or fluorinated apatite, and the like. These calcium phosphate compounds may be used separately or in combination to form the granules. Porous granules used in the present invention can be produced in accordance with any conventional method well-known in itself, such as the method in which a foaming agent such as hydrogen peroxide is used to form pores in the granules, or the method in which the calcium phosphate compound is mixed with a particulate substance capable of being dissipated upon heating and the mixture is granurated and then heated to form the porous granules.

The porous granules used in the present invention are those fired at a temperature of 200° to 1400° C., preferably 500° to 1300° C., more preferably 700° to 1200° C. The firing at temperatures of less than 200° C. should be avoided, because the resulting granules have a low bonding strength, and therefore can be destroyed in physiological saline or blood. The destruction of the granules means that the granules can not be practically used in the chemotherapy. On the other hand, firing temperatures over 1400° C. should be also avoided, because such high temperatures cause decomposition of the calcium phosphate compound, such as hydroxyapatite.

Further, it is essential to the porous granules used in the present invention have a porosity of 0.1 to 70%, preferably 1 to 60%, more preferably 10 to 50%. A porosity of less than 0.1% is not suitable for practical uses because of an excessively reduced drug content, and that of more than 70% is inappropriate because the granules are unusable due to a reduced strength thereof.

Furthermore, it is essential to the porous granules that they have a specific surface area of 0.1 to 50 m$^2$/g, preferably 1 to 40 m$^2$/g, more preferably 10 to 30 m$^2$/g. The specific surface area of less than 0.1 m$^2$/g is not suitable for practical uses because a content of the drug component is reduced as a result of an excessively reduced surface area to be adhered with the drug component, while the specific surface area of more than 50 m$^2$/g is inappropriate because a strength of the granules is reduced to a level not enough to be used.

Moreover, to obtain a satisfactory retension capability of the drug component, the porous granules used in the present invention should preferably have a pore size of 1 nm to 10 $\mu$m, more preferably 10 nm to 8 $\mu$m, most preferably 50 nm to 5 $\mu$m. A pore size out of the above range is not preferable, because the pore size of less than 1 nm does not ensure a permeation of the drug into pores of the granules, and that of more than 10 $\mu$m does not ensure a retention of the drug in the pores.

In addition, preferably, the porous granules have a granule size of 1 $\mu$m to 10 mm. When the granules are used in the transcatheter vascular embolization, they have preferably a granule size of 5 to 1000 $\mu$m, because capillary blood vessels generally have a diameter of at least 5 $\mu$m and catheters used to apply the granules to a blood vessel generally have an inner diameter of about 1000 $\mu$m. In practice, the granules have more preferably a granule size of 5 to 500 $\mu$m, since it is ideal that the granules are retained in a vessel near to a tumor tissue to be treated. The granules have most preferably a granule size of 10 to 100 $\mu$m. On the other hand, when the granules are used as a filler, the size of the granules may vary depending upon the size of defects to be filled. A granule size of less than 1 $\mu$m is not suitable for the filler, because the granules tend to be diffused in a living body too rapidly and to be englobed by a macrophage, etc., while a granule size of more than 10 mm is not preferable, because large gaps among the granules filled in an osseous defect portion are made so that ossification can hardly occur. Therefore, the granules for use as fillers have more preferably a granule size of 5 $\mu$m to 5 mm, most preferably 10 $\mu$m to 4 mm. The granule size of the granules and a distribution of the granule size can be suitably controlled by using a pertinent granulation technology of ceramics, depending upon the desired results.

The porous granules of the present invention may have a hollow structure in which the drug component is contained. In this case, it is essential that the shells of the hollow granules have a thickness of 1/10 or more of the granule size. The hollow granules can be produced in accordance with any well-known methods, and preferably can be produced by forming a porous coating of the calcium phosphate compound around particles of a combustible substance and heating and removing the combustible substance in a process of the firing.

The slow release drug delivery granules according to the present invention can be produced by impregnating the above-described porous granules of the calcium phosphate compound with a drug component, and drying the impregnated granules.

The impregnation of the drug component can be carried out by using any conventional methods. For example, if the drug component used is a liquid, it may be used without dilution or may be used after being diluted with a diluent, with the porous granules of the calcium phosphate compound being immersed in the liquid drug component or a diluted solution thereof. If the drug component is a solid, the impregnation can be carried out by dissolving or suspending the drug component in a suitable solvent and immersing the granules in the solution or suspension. The concentration of the drug component in the diluted solution or the solution or suspension can be suitably selected depending upon a specific amount of the drug component to be impregnated into the granules, but generally, it is preferred to select the highest concentration of the drug component to ensure an impregnation of the drug component into the granules at as high a level as possible.

After the impregnation has been completed, the thus obtained granules impregnated with the drug component are dried to obtain the slow release drug delivery granules of the present invention. Drying may be carried out by using any conventional methods, for example, a heating method or a freeze-drying method. Drying by a heating method may be carried out by heating the impregnated granules in a constant temperature dryer at a temperature of 100° C. or less. However, since some drugs may be deteriorated at a high temperature, freeze-drying is preferable. Freeze-drying may be carried out by using any conventional method well-known per se. For example, the drug component-impregnated granules may be freeze-dried by freezing the granules at a temperature of $-70°$ C. or less and dehydrating the frozen product in a vacuum pan under a reduced pressure of $10^{-4}$ to $10^{-7}$ Torr.

In the slow release drug delivery granules according to the present invention, a slow release action thereof can be controlled by suitably selecting a porosity, specific surface area and pore size of the granules of the calcium phosphate compound.

In addition, if the slow release drug delivery granules are coated with a soluble, organic polymeric compound, it is possible to increase a slow release action of the drug component, while controlling a specific gravity of the granules. The control of the specific gravity of the granules is important because of the following reason:

In applications of the slow release drug delivery granules in a transvascular treatment, if the granules used have a high specific gravity, clogging of the delivery tube with the granules will result, and accordingly delivery of the drug to a desired site to be treated will be prevented. Since the particles of the calcium phosphate compound per se have a higher specific gravity than that of water, they may be coated with a substance having a lower specific gravity as compared with that of the calcium phosphate compound used, to reduce a specific gravity of the resulting slow release drug delivery granules, thereby ensuring an easy and correct delivery of the drug to the desired site.

The organic polymeric compound used as the coating substance preferably has a solubility and no toxicity to the human body, because it is desired that the coated substance be gradually dissolved in blood or humor. Usable and useful polymeric compounds include, for example, albumin, dextran, ethyl ester of iodized poppy seed oil fatty acid, gelatin, carboxymethylchitin, glycol chitin and the like.

Coating with the organic polymeric compound may be carried out in accordance with any conventional method well-known per se in the art. Suitable coating methods include, for example, (1) mixing the dried granules with the above-described organic polymeric compound or a solution thereof; (2) spraying the granules with the organic polymeric compound or a solution thereof; (3) mixing the granules with the organic polymeric compound having a particle size of 1/10 or less of the size of the granules and, if desired, a binder and water, and then stirring the mixture at a high speed. The layer thickness of the resulting coating can suitably be determined depending upon a desired specific gravity of the granules, or a desired level of the slow release effect.

In the present invention, the drugs to be impregnated into the granules are not limited to specific drugs, and include different types of the drugs, such as carcinostatics, antibiotics, and the like. And, the application of the slow release drug delivery granules is also not limited to specific methods, and include, for example, a local injection or application as an implantation tablet or a filler, in addition to the transvascular chemotheraphy.

According to the present invention, slow release drug delivery granules can be easily produced, and the drug delivery granules can exhibit an excellent slow release effect of the drug, because porous granules can contain a drug component in pores thereof. Further, a slow release effect of the granules can be freely controlled, because granule size, distribution of the granule size, porosity, specific surface area, pore size of the like of the granules can be also controlled, if desired. Furthermore, since the granules of the calcium phosphate compound are used, the drug delivery granules have no toxicity to a human body, have an excellent imaging property to an X-rays or ultrasonic waves, and can be easily traced after the application thereof. Furthermore, when the granules are coated with an organic polymeric compound, the coated granules can exhibit an improved slow release effect, and also can be suitably applied to a vascular embolization treatment, because the specific gravity of the granules can be freely controlled.

Moreover, the slow release drug delivery granules of the present invention can be applied by using any conventional methods, because the impregnation can be made with different types of the drugs, depending upon the specific application method used. For example, the granules can be suitably applied to make a treatment wherein a dissipation of the granules is desired, if a calcium phosphate compound having a high solubility, for example, tricalcium phosphate (Ca/P=1.5), is used, and also they can be applied as a filler for an osseous defect portion, if a calcium phosphate compound having a low solubility, for example, hydroxyapatite (Ca/P=1.67), is used.

The present invention will be further described with regard to the working examples thereof, but it should be noted that these examples do not restrict the scope of the present invention.

EXAMPLE 1

Porous hydroxyapatite granules having a Ca/P ratio of 1.67, average granule size of 30 $\mu$m, porosity of 50%, average pore size of 90 nm and specific surface area of 23.0 m$^2$/g, fired at a temperature of 700° C., were prepared. The hydroxyapatite granules (100 mg) were mixed with an aqueous solution of 10 mg of ADRIACIN (trade name for carcinostatic, doxorubicin sulfate, commercially available from Kyowa Hakko K. K.; hereinafter referred to as ADR) in 2 ml of water, to obtain ADRIACIN-impregnated granules. The thus obtained impregnated granules were freeze-dried at $-70°$ C. under a reduced pressure of $10^{-4}$ to $10^{-7}$ torr by using MODULYO (NISSAN-EDWARD VACUUM K. K.) and disintegrated. The obtained granules were suspended in a mixed solution of 1 ml of the iodine-type contrast medium: CONRAY (trade name for the injection solution, sodium iothalamate, commercially available from Daiichi Seiyaku K. K.) and 1 ml of LIPIODOL (trade name of an ethyl ester of iodized poppy seed oil fatty acid; commercially available from Kodama K. K.). The suspension of the granules in LIPIODOL (hereinafter referred to the suspension of the HAL granules) were thus produced.

EXAMPLE 2

Porous hydroxyapatite granules having a Ca/P ratio of 1.67, average granule size of 400 $\mu$m (granule size range of 300 to 500 $\mu$m), porosity of 40%, average pore size of 80 nm and specific surface area of 25 m$^2$/g, fired at 700° C. were impregnated with ADRIACIN, freeze-dried and disintegrated in a similar manner to Example 1 to obtain the granules impregnated with ADR.

100 ml of a 10% aqueous solution of dextran were sprayed on 50 g of the above obtained impregnated granules under stirring in a stirrer at 300 rpm and then dried at room temperature to obtain the dextran-coated granules having a coated layer of a thickness of 20 to 100 $\mu$m (in dry state).

EXAMPLE 3

5% aqueous solution of gelatin was prepared by dissolving gelatin in water at 70° C. and cooling the obtained solution to room temperature. 100 $\mu$m of the above obtained gelatin solution were sprayed on 50 g of the ADR-impregnated granules produced in Example 2 under the same stirring conditions as Example 2 and then dried at room temperature to obtain the gelatin-coated granules having a coated layer of a thickness of 50 to 200 $\mu$m (in dry state).

EXAMPLE 4

50 g of distilled water were sprayed on a mixture of 100 g of the ADR-impregnated granules produced in Example 2 and 100 g of carboxymethylchitin (average particle size of 20 $\mu$m) in a stirrer and, after stirring at a high speed of 5000 rpm, dried at room temperature to obtain the carboxymethylchitin-coated granules having a coated layer of a thickness of 100 to 300 $\mu$m (in dry state).

EXAMPLE 5

Porous tricalcium phosphate (TCP) granules having a Ca/P ratio of 1.5, average granule size of 20 $\mu$m (granule size range of 10 to 30 $\mu$m), porosity of 30%, average pore size of 500 nm and specific surface area of 4.2 m$^2$/g, fired at 1100° C. were impregnated with ADRIACIN, freeze-dried and disintegrated in a similar manner to Example 1 to obtain the ADR-impregnated granules.

A mixture of 50 g of the above obtained granules and 100 ml of 2% aqueous solution of glycol chitin was dried and disintegrated to obtain the glycol chitin-coated granules having a coated layer of a thickness of 10 to 100 $\mu$m (in dry state).

EXAMPLE 6

Hydroxyapatite powder having a Ca/P ratio of 1.67 and average particle size of 0.8 μm was mixed with spherical acryl beads having an average size of 50 μm which serve as cores of granules in a stirrer and stirred under spraying of distilled water at a high speed of 5000 rpm. The thus coated beads were fired at a temperature of 900° C. to obtain the hollow granules of hydroxyapatite having an average granule size of 90 μm (granule size range of 60 to 120 μm). These hollow granules have a porosity of 50%, average pore size of 200 nm and specific surface area of 14.5 m²/g. ADR-impregnated granules were prepared by using the above obtained hollow granules in a similar manner to Example 2.

100 ml of 5% aqueous solution of albumin were sprayed on 50 g of the above obtained hollow granules under the same stirring conditions as Example 2 and then dried at room temperature to obtain the coated granules having a coated layer of a thickness of 10 to 100 μm (in dry state).

EXPERIMENTAL EXAMPLE 1

Each 0.1 ml of the suspension of the HAL granules produced in Example 1 was injected, through a common hepatic artery thereof, into male Wistar rats of the body weight of about 200 g. After the injection of the suspension of the HAL granules, the liver was extirpated from the rats at a predetermined interval of time (immediately after injection, 6 hours after, 24 hours after, and 48 hours after) to determine an ADR amount in the liver with a high performance liquid chromatography (HPLC method). Five rats were used for each group. The results of the ADR determination are shown in the following Table 1 and Plotted in FIG. 1. Note, the ADR amount is indicated as a level (%) of the residual ADR in the liver; "100%" means the residual ADR determined immediately after the injection.

EXPERIMENTAL EXAMPLE 2

This example is a comparative example.

For comparison, the procedure of Experimental Example was repeated with the proviso that the suspension of the HAL granules were replaced with a mixture of 10 mg of ADR and 2 ml of CONRAY (hereinafter referred to as ADR mixture) or a suspension of 10 mg of ADR in a mixture of 1 ml of LIPIODOL and 1 ml of CONRAY (hereinafter referred to as ALC). The results of the ADR determination are also shown in the following Table 1 and plotted in FIG. 1.

TABLE 1

| Test material | Residual ADR (%) | | |
|---|---|---|---|
| | after 6 hr. | after 24 hr. | after 48 hr. |
| Suspension of HAL-Granules | 49.8 | 13.6 | 8.2 |
| ADR Mixture | 35.4 | 10.0 | 3.0 |
| ALC | 16.0 | 4.8 | 1.1 |

The results of Table 1 show that the suspension of the HAL granules exhibit the highest residual ADR in the liver, and after 6 hours from the injection, they can maintain a high residual ADR of 49.8%. This means that according to the present invention, a slow release effect of the drugs can be notably improved in comparison with the prior art methods.

EXPERIMENTAL EXAMPLE 3

This example is intended to explain a reduction of the hepatic dysfunction by using the suspension of the HAL granules according to the present invention. For comparison, the ADR mixture and ALC used in Experimental Example 2 were also used herein.

Figure 2:
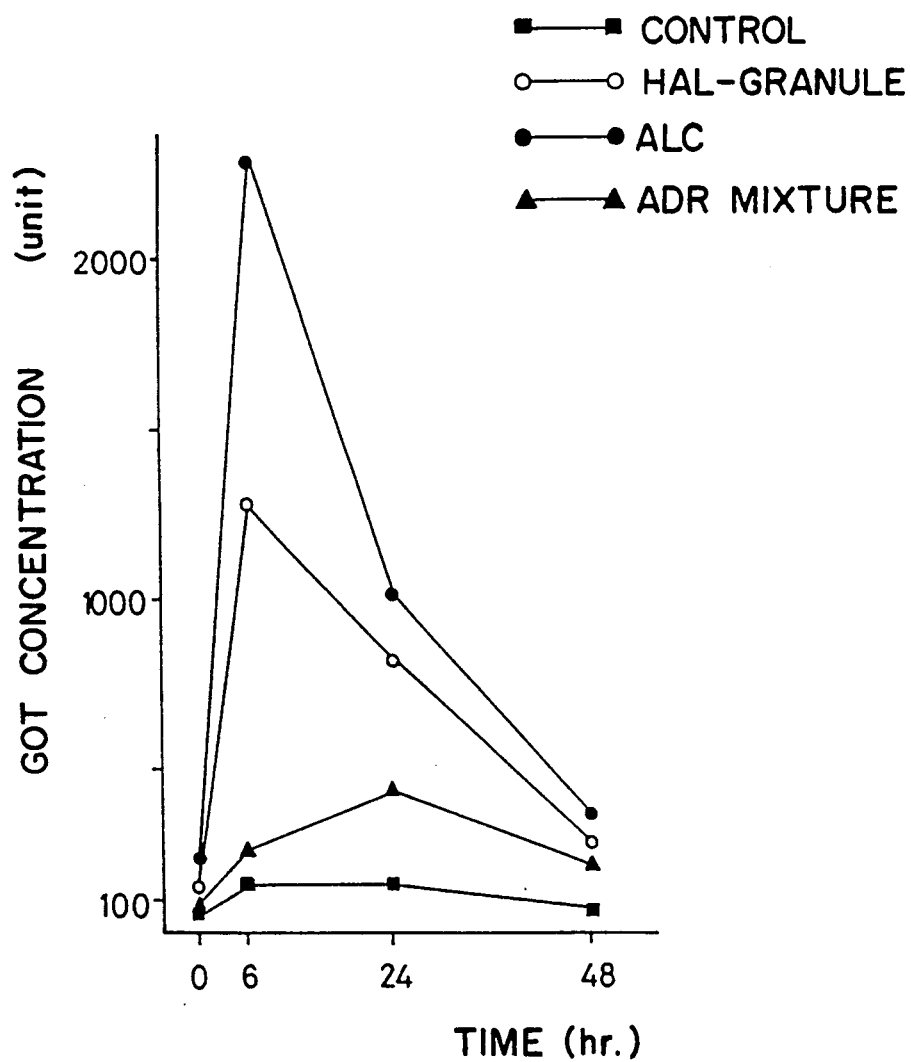
FIG. 2 is a graph showing a change of serum GOT level with time.
Figure 3:
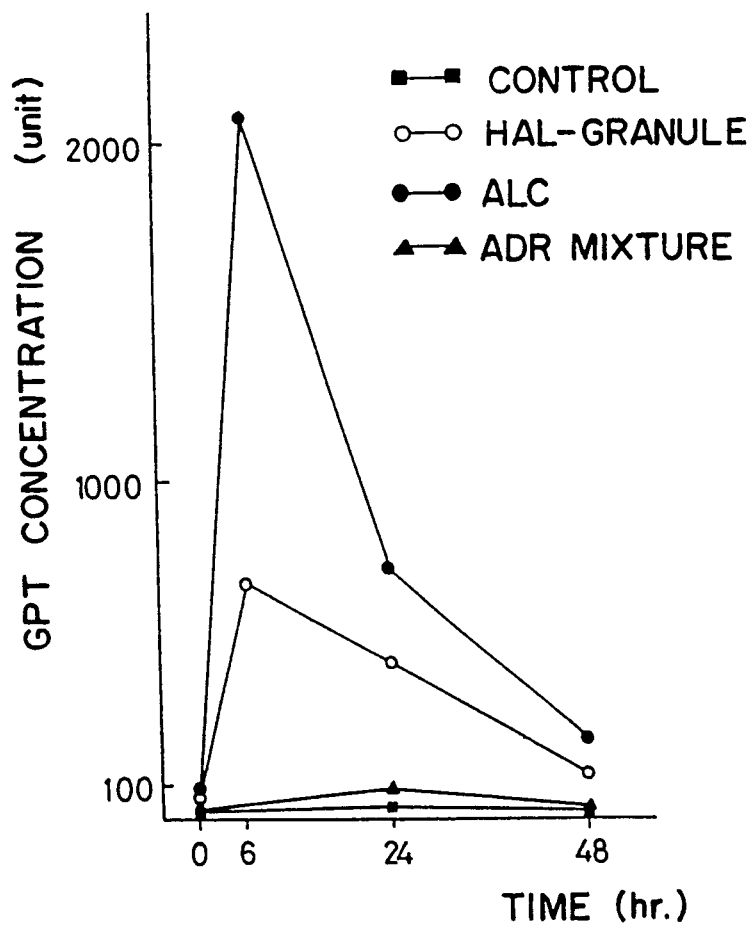
FIG. 3 is a graph showing a change of serum GPT level with time.

Each 0.1 ml of the test material (the suspension of HAL granules, ADR mixture or ALC) was injected, through a common hepatic artery thereof, into male Wistar rats of the body weight of about 200 g. Before the injection of the test material, the hepatic artery was ligated. After injection of the test material, a level of GOT (aspartate aminotransferase) or GPT (alanine aminotransferase) in the serum was determined at a predetermined interval of time (immediately after the injection, 6 hours after, 24 hours after, and 48 hours after), and the results were summarized in the following Table 2 and plotted in FIGS. 2 and 3.

As a control, the above procedure was repeated without injection of the test material. The results are also shown in Table 2 and FIGS. 2 and 3.

TABLE 2

| Test material | GOT* (unit) | GPT* (unit) |
|---|---|---|
| Suspension of HAL-Granules | 1270 | 700 |
| ADR Mixture | 420 | 80 |
| ALC | 2310 | 2090 |
| Control | 150 | 40 |

*maximum value

The results of Table 2 show that if the suspension of the HAL granules of the present invention are used, a hepatic dysfunction can be significantly reduced in comparison with the prior art method in which the ALC was used as the test material. It is considered that these satisfactory results could be obtained, because hydroxyapatite used as a granule material has a good biocompatibility and a size of the granules can be adjusted to an inner diameter of the blood vessel. The granules had a size which is the same with or is slightly larger than the inner diameter of the blood vessel.

EXAMPLE 7

50 g of porous hydroxyapatite granules having a Ca/P ratio of 1.67, granule size of 300 to 500 μm, porosity of 40%, average pore size of 80 nm and specific surface area of 25 m²/g, fired at 700° C. (used in Example 2) were added into 50 ml of brown ink (a recorder ink, available from CHUGAI KASEI K. K.) to impregnate with the dyestuff and dried in a constant temperature drier at 50° C. to obtain dyestuff-impregnated granules (hereinafter referred to as granules A).

The obtained impregnated granules were coated with dextran in a similar manner to Example 2 to produce the dextran-coated granules (hereinafter referred to as granules B).

EXAMPLE 8

50 g of the dyestuff-impregnated granules produced in Example 7 were coated with gelatin in a similar manner to Example 3 to obtain the gelatin-coated granules (hereinafter referred to as granules C).

EXAMPLE 9

100 g of the dyestuff-impregnated granules produced in Example 7 were coated with carboxymethylchitin in a similar manner to Example 4 to obtain the carboxymethylchitin-coated granules (hereinafter referred to as granules D).

EXAMPLE 10

The dyestuff-impregnated granules were produced with use of porous tricalcium phosphate (TCP) granules used in Example 5 in a similar manner to Example 7. 50 g of the obtained dyestuff-impregnated granules were coated with glycol chitin in a similar manner to Example 5 to obtain the glycol chitin-coated granules (hereinafter referred to as granules E).

EXAMPLE 11

The dyestuff-impregnated granules were produced with use of the hollow granules of hydroxyapatite obtained in Example 6 in a similar manner to Example 7 and coated with albumin in a similar manner to Example 6 to obtain the albumin-coated granules (hereinafter referred to as granules F).

EXPERIMENTAL EXAMPLE 4

Dialysis tubes (seamless cellulose tubing 8/32 available from VISKASE SALES) were filled with 1 g of each of granules A to F produced in Examples 7 to 11 and, after ligating both ends of the tubes with threads, introduced into a beaker containing 200 ml of distilled water and then stirred with a stirrer. The amount of the ink released into the distilled water was determined 1 hour after, 3 hours after, 6 hours after, 12 hours after and 24 hours after.

More specifically, the amount of the ink released from the granules was determined by removing the tubes filled with the granules after elapse of a predetermined time, evaporating water in the beaker, redissolving the ink in 10 ml of distilled water to give an aqueous solution of the ink and determining the concentration of the ink in the aqueous solution by means of a spectrophotometer (UV-100-01 available from SHIMAZU SEISAKUSHO) as a light transmittance at a wave length of 620 nm. A light transmittance of "100%" means that of distilled water.

For comparison, dialysis tubes were filled with the same dyestuff as described in Example 7 (1 ml; the amount considered to be impregnated in 1 g of the granules) and, after ligating both ends of the tubes with treads, introduced into a beaker containing 200 ml of distilled water and then stirred with a stirrer. Amount of the ink released into the distilled water was determined in the same manner as above. This experiment is carried out to obtain a control.

Figure 4:
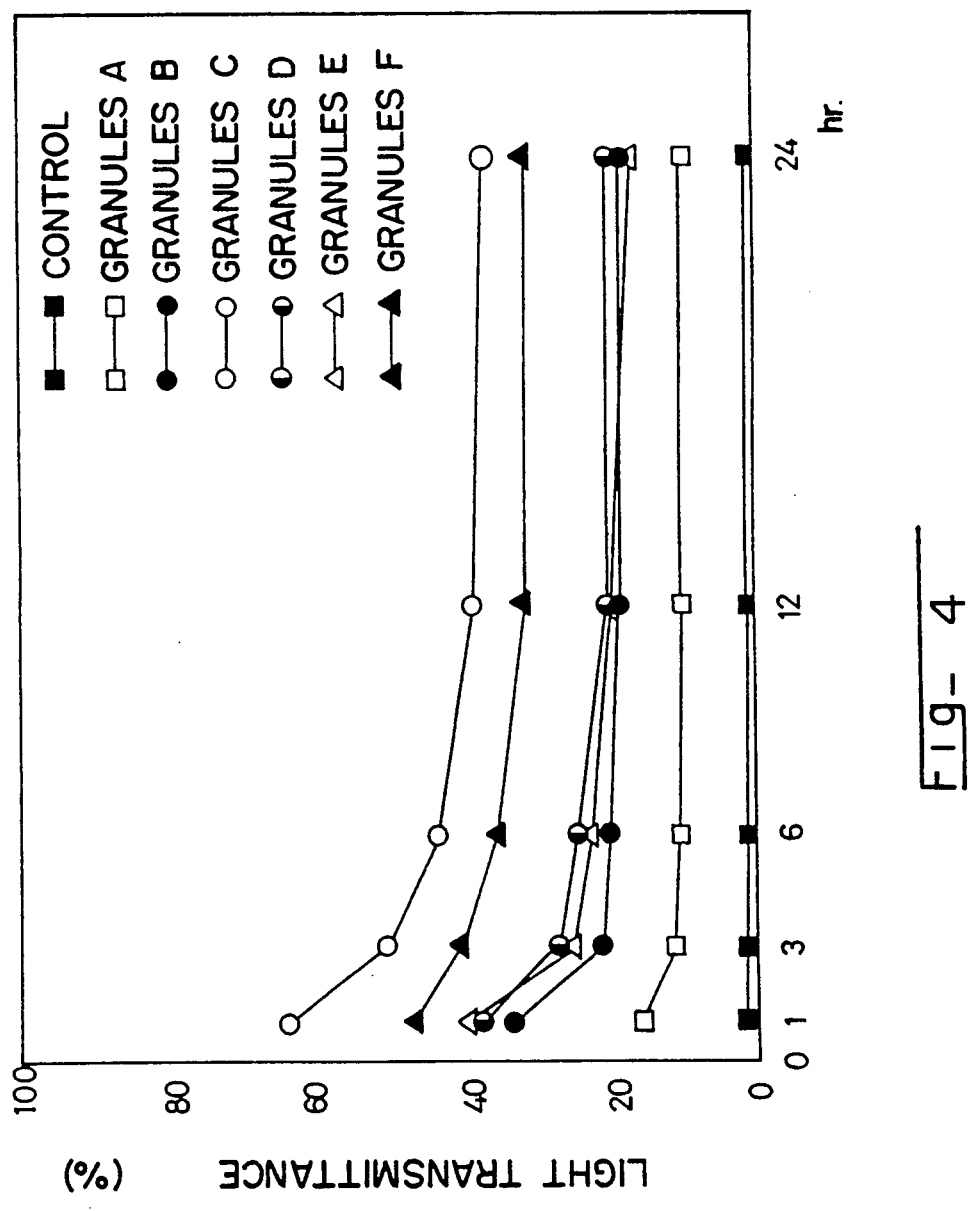
FIG. 4 is a graph showing a change of light transmittance of a solution of a dyestuff released from the granules in a dialysis tube with time.

The results of the determination were plotted in FIG. 4.

The results shown in FIG. 4 indicate that the impregnated porous calcium phosphate granules slowly release the dyestuff, the concentration of the dyestuff in the water gradually increases and the light transmittance gradually decreases thereby illustrating the effect of slow release of the drug. Furthermore, the granules coated with an organic polymeric compound show an improved slow release effect, while the rate of releasing the drug varied depending on the coating substance and the structure of the granules.

In these examples, hydroxyapatite and tricalcium phosphate were used as the calcium phosphate compound. However, it should be noted that similar and satisfactory results can be obtained with other calcium phosphate compounds such as those described above.

We claim:

1. Slow release drug delivery granules comprising porous granules of a calcium phosphate compound having an atomic ratio of Ca to P of 1.3 to 1.8, porosity of 0.1 to 70%, specific surface area of 0.1 to 50 m$^2$/g and pore size of 1 nm to 10 μm, calcined at a temperature of 200° to 1400° C., and a drug component impregnated in pores of the granules.

2. Granules according to claim 1, in which the granules have a size of 1 μm to 10 mm.

3. Granules according to claim 1, in which the granules have a hollow structure and an inner space thereof contains the drug component.

4. Granules according to anyone of claim 1, in which the granules have a coating comprising a soluble organic polymeric compound applied on a surface thereof.

5. Granules according to claim 4, in which the organic polymeric compound is selected from the group consisting of albumin, dextran, ethyl ester of iodized poppy seed oil fatty acid, gelatin, carboxymethylchitin and glycol chitin.

6. A process for the production of slow release drug delivery granules, which comprises the steps of:
impregnating porous granules of a calcium phosphate compound having an atomic ratio of Ca to P of 1.3 to 1.8, porosity of 0.1 to 70%, a specific surface area of 0.1 to 50 m$^2$/g and a pore size of 1 nm to 10 μm, fired at a temperature of 200° to 1400° C., with a drug component; and
drying the thus obtained impregnated granules.

7. A process according to claim 6, in which the granules have a size of 1 μm to 10 mm.

8. A process according to claim 6, in which the granules are impregnated with the drug component by immersing the granules in a bath containing the drug component.

9. A process according to claim 6, in which the impregnated granules are freeze-dried by freezing the granules at a temperature of −70° C. or less, and dehydrating the frozen product under a reduced pressure of 10$^{-4}$ to 10$^{-7}$ Torr.

10. A process according to claim 6, in which beads of a combustible substance are coated with the porous calcium phosphate compound, and the coated beads are heated to burn the combustible substance off, thereby producing granules having a hollow structure.

11. A process according to claim 6, which further comprises the step of coating the dried granules with a soluble, organic polymeric compound.

12. A process according to claim 11, in which the dried granules are mixed with the organic polymeric compound or an aqueous solution thereof to form a coating of the polymeric compound.

13. A process according to claim 11, in which the dried granules are spray-coated with the organic polymeric compound or an aqueous solution thereof to form a coating of the polymeric compound.

14. A process according to claim 11, in which the dried granules are mixed with the organic polymeric compound having a particle size of 1/10 or less of the size of the granules, and the mixture is stirred at a high agitation speed to form a coating of the polymeric compound.

15. A process according to claim 11, in which the organic polymeric compound is selected from the group consisting of albumin, dextran, ethyl ester of iodized poppy seed oil fatty acid, gelatin, carboxymethylchitin and glycol chitin.

16. A process according to claim 14, in which the mixture includes a binder and water.

* * * * *

UNITED STATES PATENT AND TRADEMARK OFFICE
CERTIFICATE OF CORRECTION

PATENT NO.   : 5,055,307
DATED        : October 8, 1991
INVENTOR(S)  : Sumiaki TSURU et al.

It is certified that error appears in the above-indentified patent and that said Letters Patent is hereby corrected as shown below:

Title page:   ,  Item:   [73] Assignee, at line 1, change "Kagaku" to ---Kogaku---; and at line 2, change "Kaisha, Japan" to ---Kaisha, Tokyo, Japan---.

Title page:      Item:   [56] U.S. Patent Documents, line 3, after "Reiner et al." insert ---424/425---.

At column 10, line 12 (claim 4, line 1), after "to" delete "anyone of".

Signed and Sealed this

Fifth Day of March, 1996

Attest:

BRUCE LEHMAN

*Attesting Officer*   Commissioner of Patents and Trademarks